United States Patent [19]
Karakashian

[11] 3,937,219
[45] Feb. 10, 1976

[54] STERILE SYRINGE ASSEMBLY AND METHOD OF MAKING SAME

[76] Inventor: Nubar A. Karakashian, 539 E. Allegheny Ave., Philadelphia, Pa. 19134

[22] Filed: Jan. 14, 1974

[21] Appl. No.: 433,118

[52] U.S. Cl............. 128/184; 128/218 S; 206/365; 206/439
[51] Int. Cl.² ............... A61M 5/18; A61M 5/31
[58] Field of Search............ 128/184, 218 R, 218 S, 128/215; 206/364, 365, 439

[56] References Cited
UNITED STATES PATENTS

| | | | |
|---|---|---|---|
| 2,337,347 | 12/1943 | McPherson | 128/184 |
| 2,674,998 | 4/1954 | Boehm | 128/218 R X |
| 2,887,215 | 5/1959 | Hutchison | 206/365 |
| 2,955,705 | 10/1960 | Krueger et al. | 206/365 |
| 3,093,242 | 6/1963 | Huyck et al. | 206/364 X |
| 3,112,747 | 12/1963 | Cowley | 206/365 X |
| 3,148,772 | 9/1964 | Saffir | 206/364 X |
| 3,406,686 | 10/1968 | Keller | 128/218 S UX |
| 3,677,245 | 7/1972 | Welch | 128/218 S |

Primary Examiner—Robert W. Michell
Assistant Examiner—Henry J. Recla
Attorney, Agent, or Firm—Paul Maleson; Morton J. Rosenberg

[57] ABSTRACT

A sterile syringe assembly and method of making same for providing sterile air to be injected into a patient. The syringe assembly includes a syringe mounted on a platform within an enclosure package. The syringe includes a barrel portion and a plunger which is at least partially pulled back from the barrel portion to provide an internal chamber of the barrel portion filled with sterilized air. The package enclosure is opened and the syringe plunger is actuated to inject the contained sterilized air into the patient.

13 Claims, 2 Drawing Figures

STERILE SYRINGE ASSEMBLY AND METHOD OF MAKING SAME

BACKGROUND OF THE INVENTION

1. Field of the Invention

This invention relates to the field of hyperdermic syringes. In particular this invention pertains to syringes containing medicants. More in particular, this invention relates to syringe assemblies where the syringe includes a predetermined volume of sterilized air for injection into a patient.

2. Prior Art

Syringes supplied in sterile packages are known in the art. Some prior syringes of this type are used to inject air into a patient during an operation. In many cases, such syringes are used by opening the sterile package, pulling back a syringe plunger to pull air internal to the syringe, and then injecting the air into the patient. Unfortunately, the ambient air (even in operating rooms) includes micro-organisms which render the injected air non-sterile. This increases the danger of infection to the patient and may lead to deleterious results.

In some other prior assemblies, sterile air has been inserted into the syringe by withdrawing ambient air into the syringe through a flame. This procedure has been found to be unreliable and further presents the danger of an open flame in the operating room.

SUMMARY OF THE INVENTION

A method for injecting sterile air into a patient. The initial step is providing a syringe having an internal chamber with a predetermined volume containing non-sterilized air. The syringe is packaged in a gas sterilizing enclosure and sterilized through gas sterilization. The sterilizing gas is removed from within the enclosure with the air remaining within the internal chamber being sterile. The syringe is taken from the sterilized enclosure and the sterilized air is injected into the patient.

DESCRIPTION OF THE PREFERRED EMBODIMENTS

Figure 1:
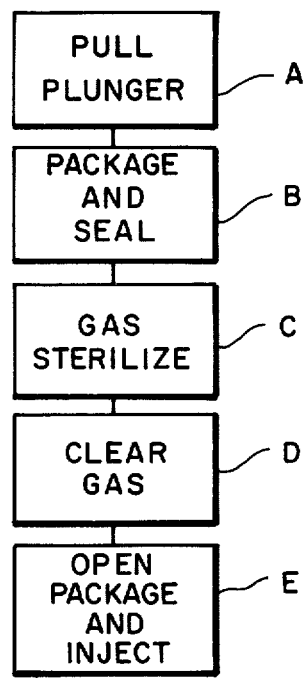
FIG. 1 is a flow block diagram showing the method for injecting sterile air into a patient; and, FIG. 2 is a perspective view, partially cut-out showing the syringe assembly.
Figure 2:
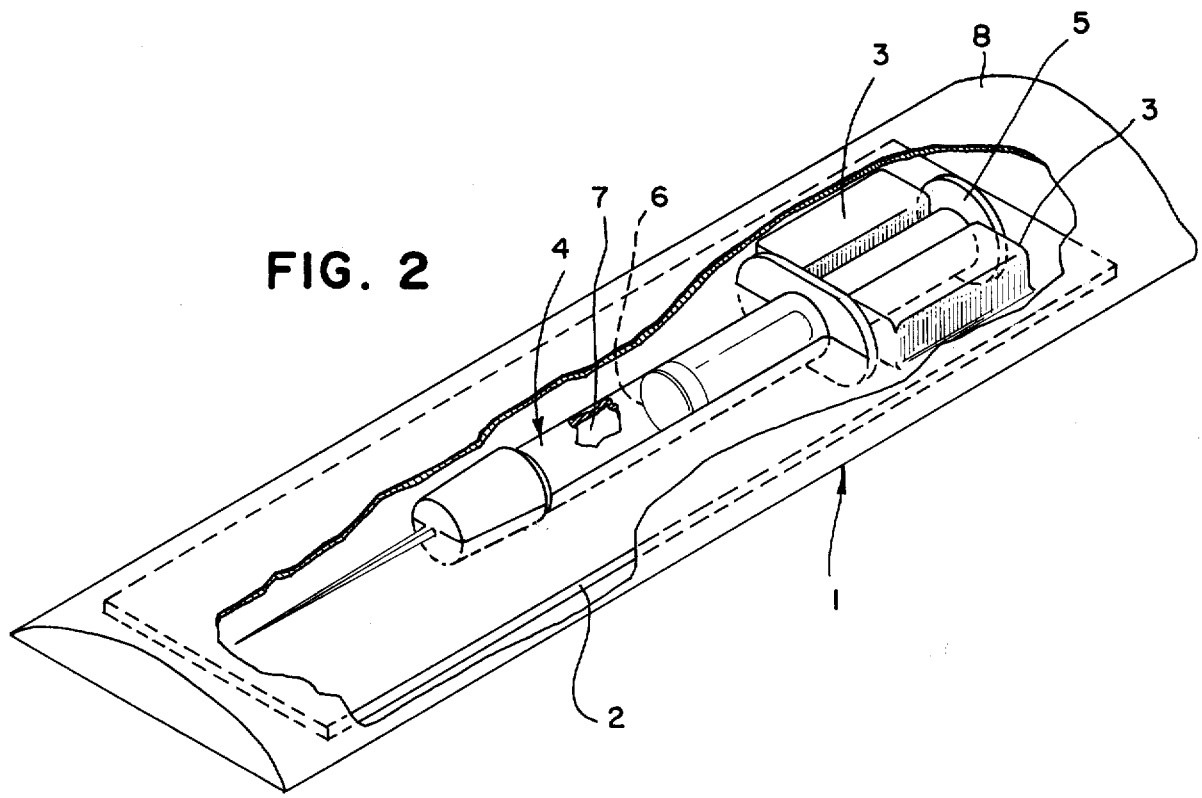

Referring now to FIGS. 1 and 2, there is shown sterile syringe assembly 1 and the block diagram associated with the method for injecting sterile air into a patient. In numerous surgical procedures, it is necessary to inject predetermined quantities of sterile air into a patient. This surgical procedure is followed in certain types of ear and eye surgery as well as in various neurosurgical operation where sterile air must be injected into the spinal cord. In such cases, the injection of the sterile air is to separate tissues to prevent adhesions. In other uses, sterile air is often injected to show organ outlines more clearly when X-Rays are being taken. It has been established that ordinary room air in an operating room environment contains micro-organisms which render the environment air non-sterile. The use of non-sterile air increases the risk of infection to the patient during the post operative time. The present invention provides both a sterile syringe assembly and associated method for injecting sterile air into a patient without regard to the operating room environment in which assembly 1 is utilized.

As shown in FIG. 2, syringe package assembly 1 includes syringe 4 having barrel portion 7 and plunger 5. Barrel portion 7 includes an internal chamber with a predetermined volume containing sterilized air. Plunger 5 includes cylinder 6 which is insertable within barrel 7 to provide the internal volume of sterilized air within syringe 4. Linear movement of plunger 5 actuates a corresponding movement of cylinder 6 to provide the internal volume displacement within barrel 7 of syringe 4. Syringe 4 is mounted on syringe platform 2 and is removeably secured thereto through insertion of syringe 4 in a syringe platform cut-out or other mechanism not important to the inventive concept as herein detailed. Both syringe platform 2 and syringe 4 are maintained within enclosure package 8 providing a seal for syringe 4 from the ambient environment.

Syringe 4 is mounted within enclosure package 8 with plunger 5 at least partially pulled back to provide a predetermined volume of sterilized air within an internal chamber formed within barrel 7. Thus, syringe platform 2 includes a mechanism for maintaining a predetermined volume of the sterilized air with the barrel portion 7 of syringe 4. This mechanism includes platform mount 3 secured to syringe platform 2 as is shown. The securement mechanism may be through adhesives, the formation of syringe platform 2 and mount 3 in one piece formation or some like technique. As is seen, mount 3 includes a predetermined longitudinal extension and has opposing displaced longitudinal surfaces for interfacing with a flange of barrel portion 7 and a second flange of plunger 5. When syringe 4 is mounted within package 8 in this manner, it is seen that first and second flange members of barrel 7 and plunger 5 respectfully are displaced each from the other by a predetermined amount. This predetermined linear displacement of the flanges provides for a predetermined internal volume of sterilized air to be maintained within the chamber of barrel 7.

In the manner disclosed, it is seen that syringe 4 may be utilized directly in an operating room whereby enclosure package 8 is open and plunger 5 is moveably displaced toward the flange section of barrel portion 7 to provide direct injection of the sterile air into the patient. Thus, the direct injection of the sterile air into the patient from syringe 4 removes the possibility that the micro-organisms in the air within the operating room will be injected internal to the patient.

The method for providing sterile syringe assembly 1 for use in injecting sterile air into the patient during an operation is shown in the flow block diagram FIG. 1. Initially, syringe 4 is provided having an internal chamber with a predetermined volume containing non-sterilized air. As is shown in flow block A, the step providing syringe 4 includes the step of displacing or pulling back syringe plunger 5 through some predetermined linear distance to provide a predetermined volume of non-sterilized air within the internal chamber of barrel 7. Although the volume provided may vary, syringes 4 often come in sizes such as 1, 3, 5, 10, 20, and 40 cubic centimeters. Thus, initially plunger 5 is pulled back through some linear distance to provide a chamber within chamber 7 of non-sterilized air having a known volume.

The next succeeding step is shown in block B where syringe 4 is packaged and sealed in gas sterilizing enclosure package 8. This step includes the mounting of syringe 4 on syringe platform 2 within enclosure 8. Thus, syringe 4 is removeably secured to platform 2 by inserting such in a cut-out or some like means. Further, the mounting of syringe 4 includes the maintaining of predetermined internal chamber volume of barrel 7 when syringe 4 is mounted within gas sterilizing enclosure 8 prior to its use in the operating room. This is accomplished by constraining a flange of plunger 5 at least a predetermined distance from flange section of barrel portion 7 of syringe 4 which in cooperation with cylinder 6 provides a predetermined necessary volume within barrel 7. This constrainment is accomplished by placing syringe 4 on platform mount 3 in a manner such that the flange on plunger 5 and the flange on barrel portion 7 are positioned contiguous to opposing linearly displaced surfaces of the platform mount. Thus, it is seen that once syringe 4 is removeably mounted or secured to syringe platform 2, that the internal volume of the chamber within barrel 7 is fixed to at least a predetermined amount. It will be noted that at this stage of the method that the air within the chamber of barrel portion 7 is still non-sterilized.

Enclosure package 8 is then sealed throughout a peripheral boundary of the enclosure contour. Package 8 may be formed of a gas permeable substance such as plastic and such may be heat sealed to provide protection from the ambient environment.

Sterile syringe assembly 1 is then sterilized through gas sterilization as is shown in flow block C of FIG. 1. Gas sterilization with ethylene oxide has received wide acceptance for materials which are sensitive to heat and moisture. It has been found to be as effective as auto-claving but is more time consuming. Often, gas sterilization is the method of choice for items that can not be steam sterilized. This method depends on the toxicity of ethylene oxide to destroy micro-organisms. Although not completely understood, it is believed that the ethylene oxide destroys the micro-organisms by alkylation which causes the replacement of the available hydrogen atom in some susceptible chemical groups in a protein molecule with its hydroxyethyl radical. Both package enclosure 8 and barrel 7 of syringe 4 are formed of an ethylene oxide permeable material such as plastic. The step C of gas sterilization includes inserting sterile syringe assembly 1 after sealing of package 8 in a sterilizing gas environment such as ethylene oxide. In this manner with package enclosure 8 and barrel 7 being gas permeable, it is seen that the sterilizing gas passes internal to syringe assembly 1.

The next consecutive step is to clear the sterilizing gas from the internal confines of assembly 1. Sterilized gas may be removed from within the enclosure by placing the enclosure 8 in an environment devoid of the sterilized gas. This allows the sterilized gas such as ethylene oxide to permeate through the walls of the enclosure to the external environment devoid of the sterilizing gas. The air remaining within the internal chamber of barrel 7 of syringe 4 is thus sterile. Other aeration techniques well known in the art may be used to clear the gas from assembly 1.

The final steps for use in injecting the sterile air now contained within barrel 7 into a patient is shown in flow block E of FIG. 1. In this flow block the surgeon or other operator takes the syringe from the sterilized enclosure and injects the sterilized air contained therein into the patient in one linear movement by bringing the flange on plunger 5 toward the flange of barrel portion 7 through a predetermined distance.

Other ways to provide the syringe, pre-loaded with a measured, clinically useful quantity of sterilized air, ready to be used by a medical doctor, may be mentioned. A syringe may be manufactured, complete with needle, and with plunger in the depressed condition. It may be sterilized before packaging in any known way, such as by known gas, chemical or heat. Then, maintained in a suitably sterile environment, it is loaded with a measured clinically useful volume of pre-sterilized air, for example 20 cc.

A relatively large container of air, sufficient to supply a large plurality of syringes, for example, thousands, is prepared. The air is sterilized by any known means, for example, heat. Each sterilized syringe, prepared as above, is brought in turn to the air container. The interior of each syringe barrel is connected to the air container in turn. The plunger is withdrawn to the desired mark. This draws the desired volume of air into the barrel. The connection may be made by contacting the end of the needle to a valved opening in the air container, or it may be made by providing the air container with a self-sealing membrane which may be punctured by each needle. The needles are then further maintained in a suitably sterile environment and are hermetically sealed into sterile packages to make an assembly suitable for shipment ultimately to a medical user.

The air loading as described immediately above may be done by mechanical handling in a closed chamber.

The method and means for preparing the syringe, as described immediately above are probably more expensive than the method and means first described herein.

In the manner herein described, there is provided a totally enclosed syringe assembly 1 which provides a surgeon with sterile air to be injected into a patient during an operation. In the above description of the invention specific examples have been used for illustrative purposes. It is understood that those skilled in the art can make certain modifications to these specific examples without departing from the spirit and scope of this invention.

What is claimed is:

1. A method for injecting sterile air into a patient including the steps of:
   a. providing a syringe having an internal chamber with a predetermined volume containing non-sterilized air by initially displacing a syringe plunger through a predetermined linear distance to provide said predetermined volume quantity of said non-sterilized air within said internal chamber;
   b. packaging said syringe in a gas sterilizing enclosure;
   c. maintaining said predetermined internal chamber volume when said syringe is packaged in said gas sterilized enclosure by constraining said syringe plunger a predetermined distance from a flange section of a barrel portion of said syringe;
   d. sterilizing said enclosure, said syringe, and said predetermined volume through gas sterilization;
   e. removing said sterilizing gas from within said enclosure, said predetermined volume quantity of said air remaining within said internal chamber being sterile;
   f. taking said syringe from said sterilized enclosure; and, g. injecting said predetermined volume quantity of said sterilized air contained within said internal chamber into said patient.

2. The method for injecting sterile air as recited in claim 1 where said internal chamber predetermined volume is a predetermined value within the range of 1.0 to 40.0 cubic centimeters.

3. The method for injecting sterile air as recited in claim 1 where the step of packaging said syringe includes the step of sealing said syringe within said gas sterilizing enclosure throughout a peripheral boundary of said enclosure.

4. The method for injecting sterile air as recited in claim 3 where the step of sealing said syringe includes the step of heat sealing opposing surfaces of said enclosure each to the other throughout said peripheral boundary of said enclosure.

5. The method for injecting sterile air as recited in claim 1 where the step of packaging said syringe includes the step of mounting said syringe on a platform within said enclosure.

6. The method for injecting sterile air as recited in claim 5 where the step of mounting said syringe includes the step of removeably securing said syringe to said platform within said chamber.

7. The method for injecting sterile air as recited in claim 1 where the step of constraining includes the step of placing said syringe on a platform mount secured to said platform, said syringe plunger and said flange section being positioned contiguous to opposing linearly displaced surfaces of said platform mount.

8. The method for injecting sterile air as recited in claim 1 where the step of sterilizing includes the step of inserting said enclosure in a sterilizing gas environment.

9. The method for injecting sterile air as recited in claim 8 where the step of inserting includes the step of passing said sterilizing gas internal to said enclosure.

10. The method for injecting sterile air as recited in claim 9 where said enclosure is permeable to said sterilizing gas.

11. The method for injecting sterile air as recited in claim 10 where said sterilizing gas is ethylene oxide.

12. The method for injecting sterile air as recited in claim 1 where the step of removing said sterilizing gas includes the step of placing said enclosure in an environment devoid of said sterilized gas.

13. The method for injecting sterile air as recited in claim 12 where the step of placing said enclosure includes the step of permitting said sterilizing gas to permeate through the walls of said enclosure to said environment devoid of said sterilized gas.

* * * * *